(12) United States Patent
Müllner et al.

(10) Patent No.: US 10,060,911 B2
(45) Date of Patent: Aug. 28, 2018

(54) METHOD FOR DIAGNOSIS OF HIGH-AFFINITY BINDERS AND MARKER SEQUENCES

(75) Inventors: Stefan Müllner, Langenfeld (DE); Peter Schulz-Knappe, Hemmingen (DE); Angelika Lueking, Bochum (DE); Heike Göhler, Bochum (DE); Jessica Schwermann, Dortmund (DE)

(73) Assignee: Protagen Aktiengesellschaft, Dortmund (DE)

( * ) Notice: Subject to any disclaimer, the term of this patent is extended or adjusted under 35 U.S.C. 154(b) by 792 days.

(21) Appl. No.: 14/239,224

(22) PCT Filed: Aug. 18, 2012

(86) PCT No.: PCT/EP2012/066152
§ 371 (c)(1),
(2), (4) Date: Jul. 1, 2014

(87) PCT Pub. No.: WO2013/026807
PCT Pub. Date: Feb. 28, 2013

(65) Prior Publication Data
US 2014/0309133 A1    Oct. 16, 2014

(30) Foreign Application Priority Data

Aug. 19, 2011 (DE) .................. 10 1011 081 293
Dec. 6, 2011 (DE) .................. 10 2011 087 841

(51) Int. Cl.
| | | |
|---|---|---|
| G01N 33/53 | (2006.01) | |
| G01N 33/543 | (2006.01) | |
| G01N 33/68 | (2006.01) | |
| G01N 33/564 | (2006.01) | |

(52) U.S. Cl.
CPC ..... *G01N 33/54306* (2013.01); *G01N 33/564* (2013.01); *G01N 33/6845* (2013.01); *G01N 33/6854* (2013.01)

(58) Field of Classification Search
None
See application file for complete search history.

(56) References Cited

U.S. PATENT DOCUMENTS

| | | | | |
|---|---|---|---|---|
| 5,888,749 A * | 3/1999 | Soe | ............ | C07K 16/38 435/13 |
| 6,004,743 A * | 12/1999 | Kenyon | ............ | G01N 33/5375 210/515 |
| 8,338,188 B2 * | 12/2012 | Roudier | ............ | G01N 33/6893 435/7.1 |
| 2002/0019048 A1 * | 2/2002 | Berenson | ............ | C12N 5/0636 435/372 |
| 2005/0019843 A1 | 1/2005 | Chen et al. | | |
| 2006/0127963 A1 * | 6/2006 | Lebrun | ............ | C07K 14/4713 435/7.92 |
| 2009/0075832 A1 * | 3/2009 | Neuman | ............ | C07K 7/08 506/9 |
| 2013/0217591 A1 | 8/2013 | Meyer et al. | | |
| 2013/0303395 A1 | 11/2013 | Lueking et al. | | |

FOREIGN PATENT DOCUMENTS

| | | |
|---|---|---|
| EP | 2441848 A1 | 4/2012 |
| WO | WO-99/57311 A2 | 11/1999 |
| WO | WO-99/57312 A1 | 11/1999 |
| WO | WO-2010000874 A2 | 1/2010 |
| WO | WO-2011038138 A1 | 3/2011 |

OTHER PUBLICATIONS

Hemmila (J. Alloys and Compounds 1995 vol. 225 p. 480-485).*
English Translation of the International Search Report for PCT/EP2012/066152 dated Dec. 6, 2012.
McBride, Jeffrey D. et al., "Screening autoantibody profiles in systemic rheumatic disease with a diagnostic protein microarray that uses a filtration-assisted nanodot array luminometric immunoassay (NALIA)", Clinical Chemistry, May 1, 2008, vol. 54, No. 5, pp. 883-890, American Association for Clinical Chemistry, Washington, DC USA.
Robinson, W. H. et al., "Automantigen microarrays for multiplex characterization of autoantibody responses", Nature Medicine, Mar. 1, 2002, vol. 8, No. 3, pp. 295-301, Nature Publishing Group, New York, NY USA.
International Preliminary Report on Patentability and English Translation thereof issued in PCT/EP2012/066152 dated Feb. 25, 2014.

* cited by examiner

*Primary Examiner* — Changhwa J Cheu
(74) *Attorney, Agent, or Firm* — Drinker Biddle & Reath LLP

(57) ABSTRACT

The present invention relates to a novel method for diagnosing high-affinity binders, in particular antibodies or autoantibodies, and the identification, characterization and selection of marker sequences and diagnostic use thereof, in particular in the form of a panel. The invention also relates to a singleplex assay in which the discovered selection of marker sequences is used in the form of a panel and high-affinity binders are detected using a single signal.

15 Claims, 11 Drawing Sheets

METHOD FOR DIAGNOSIS OF HIGH-AFFINITY BINDERS AND MARKER SEQUENCES

CROSS-REFERENCE TO RELATED APPLICATIONS

This application is a national stage application (under 35 U.S.C. § 371) of PCT/EP2012/066152, filed Aug. 18, 2012, which claims benefit of German application 10 2011 081 293.8, filed Aug. 19, 2011, and German application 10 2011 087 841.6, filed Dec. 6, 2011.

FIELD OF THE INVENTION

The present invention relates so a novel method for diagnosis of high-affinity binders, in particular antibodies and/or autoantibodies, and the identification, characterisation and selection of marker sequences, and diagnostic use thereof, in particular in the form of a panel. The invention also relates to a singleplex assay in which a discovered selection of marker sequences is used in the form of a panel and high-affinity binders are detected using a single signal.

BACKGROUND OF THE INVENTION

Protein biochips are gaining in significance on an industrial scale in analytics and diagnostics and also in pharmaceutical development. Protein biochips have become established as screening tools.

Here, the rapid and highly parallel detection of a large number of specific binding analysis molecules is made possible in a single experiment. To produce protein biochips, it is necessary to have the required proteins available. In particular, protein expression libraries have become established for this purpose. The high-throughput cloning of defined open reading frames is one possibility (Heyman, P. A., Cornthwaite, P., Foncerrada, L., Gilmore, P. R., Gontang, E., Hartman, K. P., Hernandez, C. L., Hood, R., Hull, H. M., Lee, W. Y., Marcii, R., Marsh, E. J., Mudd, K. M., Patina, M. J., Purcell, T. P., Rowland, P. P., Sindici, M. L. and Hoeffler, P. P. (1999) Genome-scale cloning and expression of individual open reading frames using topoisomerase I-mediated ligation. *Genome Res*, 9, 383-392; Kersten, B., Feilner, T., Kramer, A., Wehrmeyer, S., Possling, A., Witt, I., Zanor, N. I., Stracke, R., Lueking, A., Kreutzberger, J., Lehrach, H. and Cahill, D. J. (2003) Generation of *Arabidopsis* protein chip for antibody and serum screening. *Plant Molecular Biology*, 52, 999-1010; Reboul, J., Vaglio, P., Rual, J. F., Lamesch, P., Martinez, M., Armstrong, C. M., Li, S., Jacotot, L., Bertin, N., Janky, R., Moore, T., Hudson, J. R., Jr., Hartley, J. L. Brasch, M. A., Vandenhaute, J., Boulton, S., Endres C. A. Jenna, S., Chevet, E., Papasotiropoulos, V., Tolias, P. P., Ptacek, J., Snyder, M., Huang, R., Chance, M. R., Lee, H., Doucette-Stamm, L., Hill, D. E. and Vidal, M. (2003) *C. elegans* ORFeome version 1.1: experimental verification of the genome annotation and resource for proteome-scale protein expression. *Nat Genet*, 34, 35-41.; Walhout, A. J., Temple, G. F., Brasch, M. A., Hartley, J. L., Lorson, M. A., van den Heuvel, S. and Vidal, M. (2000) GATEWAY recombinational cloning: application to the cloning of large numbers of open reading frames or ORFeomes. *Methods Enzymol*, 328, 575-592). However, such an approach is closely linked to the progress of the genome sequencing projects and the annotation of these gene sequences. In addition, the determination of the expressed sequence is not always clear clue to differential splicing processes. This problem can be avoided by the use of cDNA expression libraries (Büssow, K., Cahill, D., Nietfeld, H. Bancroft, D. Scherzinger, E., Lehrach, H. and Walter, G. (1998) A method for global protein expression and antibody screening on high-density filters of an arrayed cDNA library. *Nucleic Acids Research*, 26, 5007-5008; Büssow, K., Nordhoff, E., Lübbert, C., Lehrach, H. and Walter, G. (2000) A human cDNA library for high-throughput protein expression screening. *Genomics*, 65, 1-8; Holz, C., Lueking, A., Bovekamp, L., Gutjahr, C., Bolotina, N., Lehrach, H. and Cahill, D. J. (2001) A human cDNA expression library in yeast enriched for open reading frames. *Genome Res*, 11, 1730-1735; Lueking, A., Holz, C., Gotthold, C., Lehrach, H. and Cahill, D. (2000) A system for dual protein expression in *Pichia pastoris* and *Escherichia coli*, *Protein Expr. Purif.*, 20, 372-378). Here, the cDNA of a specific tissue is cloned into a bacterial or eukaryotic expression vector, such as yeast. The vectors used for the expression are generally characterised in that they carry inducible promoters, with which the moment of protein expression can be controlled. In addition, expression vectors have sequences for what are known as affinity epitopes or affinity proteins, which on the one hand allow the specific detection of the recombinant fusion proteins by means of an antibody directed against the affinity epitope, and on the other hand enable specific purification via affinity chromatography (IMAC).

For example, the gene products of a cDNA expression library from human foetal brain tissue were arranged in the bacterial expression system. *Escherichia coli* in high-density format on a membrane and were able to be screened successfully with different antibodies. It was possible to demonstrate that the proportion of full-length proteins is at least 66%. The recombinant proteins from expression libraries could also be expressed and purified in high throughput. (Braun P., Hu, Y., Shen, B., Halleck, A., Koundinya, M., Harlow, E. and LaBaer, J. (2002) Proteome-scale purification of human proteins from bacteria, *Proc Natl Acad Sci USA*, 99, 2654-2659; BCssow (2000) supra; tucking, A., Horn, M., Eickhoff, H., Büssow, K., Lehrach, H. and Walter, G. (1999) Protein microarrays for gene expression and antibody screening. *Analytical Biochemistry*, 270, 103-111). WO 99/57311 and WO 99/57312 relate in particular to such protein biochips based on cDNA expression libraries.

Furthermore, besides antigen-presenting protein biochips, antibody-presenting arrangements are also described (Pal et al (2002) Antibody arrays: An embryonic but rapidly growing technology, DDT, 7, 143-149; Kusnezow et al, (2003), Antibody microarrays: An evaluation of production parameters, Proteomics 254-264).

There is a high demand however to improve the diagnosis of high-affinity binders, in particular antibodies, autoantibodies and marker sequences.

Protein biochips of the type described by the applicant are already described and allow the diagnosis of illnesses, in particular autoimmune diseases, on the basis of the identification of marker sequences.

WO2010/000874, in the name of the applicant, for example describes the diagnosis of prostate carcinoma and prostate inflammation by means of a protein biochip and provides specific diagnostic marker sequences.

In this case, these marker sequences for the respective indications were able to be identified sensitively for the first time by means of protein biochips.

Protein biochips allow the advantageous assignment of individual high-density loci (spots) to the respective marker sequences and signals.

For example, a high-affinity binder from a sample can be added to a protein biochip and the interaction between a high-affinity binder and a marker sequence in an environment containing various marker sequences can be detected. This is likewise possible with an array, wherein marker sequences are arranged at individual spots (loci).

Diagnostic questions can also be dealt with in this way depending on the selection of marker sequences and the high-affinity binder used. In particular, diagnosis methods are of interest in which a test subject or patient provides a sample containing high-affinity binders and the sample is exposed to an array comprising selected marker sequences for the diagnosis of a question or of an event (for example condition, illness, etc.).

There is a high demand however to simplify such methods and to minimise, in particular miniaturise, such methods.

A plurality of marker sequences can generally be used for a specific diagnostic question, and what are known as "marker panels" are used for improved handling of diagnostic questions or events. For example, marker sequences known from the literature are combined with one another in the prior art such that increased validity can be achieved.

BRIEF SUMMARY OF THE INVENTION

One object of the present invention is therefore to provide improved diagnosis methods and diagnostic use thereof, such that suitable panels of marker sequences can be provided.

A further object relates to the identification and/or characterisation and/or selection of marker sequences, such that suitable panels of marker sequences can be provided.

DETAILED DESCRIPTION OF THE INVENTION

The object is achieved by methods for the identification and/or characterisation and/or selection of marker sequences, comprising the following steps:

a.) n placed marker sequences are mixed on a solid substrate with a sample containing high-affinity binders, and an interaction is detected by means of signals, b.) at least n−1 placed marker sequences having sufficient signal intensity from a.) are mixed on a substrate with an identical sample containing high-affinity binders, and an interaction is detected by means of signals, c.) step b.) is optionally repeated with at least n−k marker sequences, wherein k≥1, d.) n−k selected marker sequences are applied to a substrate jointly at a locus and are mixed with an identical sample, and an interaction is detected by means of a single signal.

The above method will be referred to hereinafter as the "method according to the invention".

The number of marker sequences that are used in the method according to the invention is denoted by "n".

Theoretically, any number of marker sequences can be used. The number is only limited by practical feasibility (for example size of the solid substrate, used cDNA bank). For example, 50,000 or 100,000 or more marker sequences can be used in step a.) of the method according to the invention. The use of 50,000, 40,000, 30,000, 20,000, 10,000, 5,000, 1,000 or fewer marker sequences in step a.) of the method according to the invention is preferred.

With given n of 5,000, k is preferably a value from 1 to 1,000, in particular 10 to 500. For example, a significance of 90, 95 or 99 or 99.9% of the signal intensities can be set, such that such marker sequences are sufficiently considered and selected in step b.). Step c.) may also be repeated a number of times.

n is representative of a totality of marker sequences on a solid substrate. Step b.) of the method according to the invention and, where applicable, repetition of this step in accordance with step c.) is then carried out, whereby marker sequences having sufficient signal intensity and sufficient interaction with the high-affinity binders are selected. The markers that do not have sufficient signal intensity or sufficient interaction with the high-affinity binders remain unconsidered here in the further method steps. For method steps b.) and c.), only n−1 or n−k maker sequences are therefore used, wherein k≥1, and wherein preferably k<n. In a specific embodiment of the invention, "z" specific marker sequences can thus be obtained from a single method for example, wherein n−k=z. In another specific embodiment of the method, the specific marker sequences "z" can be obtained by a plurality of methods carried out independently of one another.

As a result, by means of the method according to the invention, a panel of specific marker sequences having sufficient sensitivity is obtained.

Particularly advantageously, it is possible to obtain panels of marker sequences that are applied particularly preferably in accordance with the invention to a locus or spot on an array, such that this panel of marker sequences can emit a single signal.

Surprisingly, particularly effective panels of marker sequences that ensure a single signal with significant signal intensity can thus be obtained. This is particularly advantageous if different signals with different signal intensities are present on an array. On the other hand, "a 1-locus signal" (single signal) for a panel of marker sequences allows sufficient miniaturisation and simplification or the diagnosis, such that z signal intensities of z marker sequences do not have to be established, but merely one signal intensity of the individually localised panel of z marker sequences. This is also advantageous for the signal-noise ratio within the scope of evaluation, in particular by means of algorithmic methods.

A single signal may be, for example, the mean value or the median of the measured or calculated signal intensities of the individual marker sequences in the panel.

The provision of such panels with marker sequences additionally allows a reliable diagnosis of an event, of a test subject (for example condition, illness) and/or stratification of patients with a disease.

"Diagnosis" in the context of this invention means the positive identification of an interaction between marker sequences and high-affinity binders, in particular antibodies or autoantibodies. Furthermore, an event can be indicated due to this interaction. The event is preferably the evidence of an illness or a condition of a test subject or patient. The term "diagnosis" includes medical diagnosis and related tests, in particular in-vitro diagnosis and laboratory diagnosis.

"Stratification or therapy control" within the context of this invention means that the method according to the invention allows decisions concerning the treatment and therapy of the patient, whether this be the hospitalisation of the patient, use, effect and/or dosing of one or more drugs, a therapeutic measure, or the monitoring of the progression of an illness and the progression of treatment or aetiology, or classification of a disease, for example into a new or existing sub-type, or the differentiation of illnesses and patients suffering therefrom. In particular, personalised medicine is also included.

In a further embodiment of the invention, the term "stratification" in particular includes risk stratification with the prognosis of an "outcome" of a disadvantageous health event.

Within the scope of this invention, a "patient" is understood to be any test subject (human or mammal).

The term "marker sequences" within the context of this invention includes molecules that can be identified by means of high-affinity binders. In particular, sequences such as mRNA, si-RNA, micro-RNA, cDNA, peptide or protein, in particular antigens or autoantigens, are therefore included, although this list is not exhaustive. The marker sequences may originate from an expression library, in particular including an mRNA, si-RNA, micro-RNA, cDNA, peptide or protein expression library. Furthermore, the marker sequences can be obtained from any biological material, such as tissue, native sources, cells, bacteria, viruses, phages, prions, plants, animals, humans, etc., although this list is not exhaustive. The marker sequences are preferably purified and, where necessary, isolated by conventional methods.

These marker sequences bind significantly to a high-affinity binder and have a significant interaction with the high-affinity binder. For example, the cDNA or the polypeptide or protein obtainable therefrom may interact with substances from the bodily fluid or tissue extract of a patient suffering from a disease (for example antigen (epitope) antibody (paratope) interaction).

Such an interaction is, for example, a binding to at least one marker sequence, or, in the case of a cDNA, the hybridisation with a suitable substance under selected conditions, in particular stringent conditions (for example as defined conventionally in J. Sambrook, E. F. Fritsch, T. Maniatis (1989), Molecular cloning: A laboratory manual, 2nd Edition, Cold Spring Harbor Laboratory Press, Cold. Spring Harbor, USA or Ausubel, "Current Protocols in Molecular Biology", Green Publishing Associates and Wiley Interscience, N.Y. (1989)). An example for stringent hybridisation conditions is: hybridisation in 4×SSC at 65° C. (alternatively in 50% formamide and 4×SSC at 42° C.), followed by a number of washing steps in 0.1×SSC at 65° C. for a total of approximately one hour. An example for less stringent hybridisation conditions is hybridisation in 4×SSC at 37° C., followed by a number of washing steps in 1×SSC at room temperature.

Within the scope of this invention, a "high-affinity binder" is a binder that binds specifically to a "marker sequence" or is addressed specifically to such a "marker sequence", preferably binders such as antibodies or autoantibodies. Antibodies bind specifically via one or more antigen-binding regions to one or more epitopes of the marker sequence in accordance with she key-lock principle and thus form a significant interaction within she meaning of the invention.

Within the meaning of the invention, a specific interaction is present for example if the disassociation constant of high affinity binder and marker sequence is in the picomolar or nanomolar range.

Such high-affinity binders, in particular (auto)antibodies, are preferably, in accordance with the invention, part of a sample from a patient/test subject, for example a sample of bodily fluid, in particular blood, whole blood, blood plasma, blood serum, patient serum, urine, cerebrospinal fluid, synovial fluid or a tissue extract of the patient.

In a further embodiment of the invention, the "marker sequences" have an identification signal that is addressed to the substance to be bound (for example antibody, nucleic acid). In accordance with the invention, the identification signal for a protein is preferably an epitope and/or paratope and/or hapten, and for a cDNA is preferably a hybridisation or binding region and/or an aptamer.

In accordance with the invention, the marker sequences also include modifications of a cDNA sequence or an amino acid sequence, such as chemical modifications, in particular citrullination, acetylation, phosphorylation, glycosylation, or polyA strand and further modifications well known to a person skilled in the art.

In a further embodiment of the invention, partial sequences or fragments of known marker sequences (for example SWISSProt, databases, etc.) are also included. In particular, such partial sequences have an identity of 95%, 90%, in particular 80% or 70%, with the known marker sequences.

In a further embodiment, the respective marker sequences can be represented in different quantities in one or more regions on a solid substrate. This allows a variation of the sensitivity. The regions may each comprise a totality of marker sequences, that is to say a sufficient number of different marker sequences, in particular 2 to 5 or 10 or more, and, where applicable, further nucleic acids and/or proteins, in particular biomarkers. At least 96 to 25,000 (numerically) or more however from different or identical marker sequences and further nucleic acids and/or proteins, in particular biomarkers, are preferred. Further preferably, more than 2,500, particularly preferably 10,000 or more, are different or identical marker sequences and, where applicable, further nucleic acids and/or proteins, in particular biomarkers.

Furthermore, it is essential to the invention that at least one spot or locus has a panel of marker sequences, for example 10 or more, preferably 5, 6 or 7, particularly preferably 2, 3 or 4 marker sequences.

Within the scope of this invention, the term "arrangement." is synonymous with the term "array", and, in so far as this "array" is used for the identification of substances at marker sequences, an "assay" or a diagnostic device is to be understood by this term. In a preferred embodiment, the arrangement is designed in such a way that the marker sequences represented on the arrangement are present in the form of a grid on a fixed substrate. Furthermore, such arrangements that allow a high-density arrangement of marker sequences are preferred and the marker sequences are arranged in spots. Such high-density spotted arrangements are disclosed for example in WO 99/57311 and WO 99/57312 and may advantageously be used in a robot-assisted automated high-throughput method.

Within the scope of this invention the term "assay" or diagnostic device also includes however embodiments of a device such as ELISA, Bead-based Assay, Line Assay, Western Blot, immunochromatographic methods (for example what are known as Lateral Flow Immunoassays) or similar immunological single or multiplex detection methods. A protein biochip within the meaning of this invention is the systematic arrangement of proteins on a solid substrate.

The marker sequences of the arrangement are fixed on a solid substrate, but are preferably arranged in spots or are immobilised and even imprinted, that is to say applied reproducibly. One or more marker sequences may be present a number of times in the totality of all marker sequences and may be present in different quantities based on a spot.

Furthermore, the marker sequences on the solid substrate may be standardised (for example by means of a series of dilutions, for example of human globulins as internal calibrators for data standardisation and quantitative evaluation).

In a further embodiment, the marker sequences are present as clones. Such clones can be obtained for example by means of a cDNA expression library according to the invention (Büssow et al. 1998 (supra)). In a preferred embodiment, such expression libraries containing clones are obtained by means of expression vectors from an expressing cDNA library consisting of the cDNA marker sequences. These expression vectors preferably contain inducible promoters. The expression can be induced for example by means of an inducer, such as IPTG. Suitable expression vectors are described in Terpe et al. (Terpe T Appl Microbial Biotechnol. 2003 January; 60(5):523-33).

Expression libraries are known to a person skilled in the art and can be produced in accordance with standard works, such as Sambrook et al, "Molecular Cloning, A laboratory handbook", 2nd edition (1989), CSH press, Cold Spring Harbor, N.Y. Furthermore, such expression libraries that are tissue-specific (for example human tissue, in particular human organs) are preferred. Furthermore, such expression libraries that can be obtained by means of exon-trapping are also included in accordance with the invention. Instead of expression library, reference can be made synonymously to an expression bank.

Furthermore, protein biochips or corresponding expression libraries that have no redundancy (what is known as a Uniclone® library) and that can be produced for example in accordance with the teachings of WO 9957311 and WO 9957312 are preferred. These preferred. Uniclone libraries have a high proportion of non-defective fully expressed proteins of a cDNA expression library.

Within the scope of this invention, the clones likewise may be transformed bacteria, recombinant phages or transformed cells of mammals, insects, fungi, yeasts or plants, although this list is not exhaustive.

The clones are fixed, arranged in spots, or immobilised on a solid substrate

The invention therefore relates so an arrangement, wherein the marker sequences are present as clones.

In addition, the marker sequences in the respective form may be present in the form of a fusion protein which for example contains at least one affinity epitope or "tag". The tag may be, for example, c-myc, His-tag, Arg-tag, FLAG, alkaline phosphatase, V5-tag, 17-tag or may contain Strep-tag, HAT-tag, NusA, S-tag, SBP-tag, thioredoxin, DsbA, a fusion protein, preferably a cellulose-binding domain, green fluorescent protein, malto-binding protein, calmodulin-binding protein, glutathione S-transferase or lacZ.

In all embodiments, the term "solid substrate" includes forms such as a filter, a membrane, a magnetic or fluorophore labelled bead, a silicon wafer, glass, metal, plastic, a chip, a mass spectrometry target or a matrix. A filter is preferred in accordance with the invention however.

Furthermore, PVDF, nitrocellulose or nylon are preferred as a filter (for example Immobilon P Millipore, Protran Whatman, Hybond N+ Amersham).

In a further preferred embodiment of the arrangement according to the invention, this arrangement corresponds to a grid that is the size of microtiter plate (8-12 well strips, 96 wells, 384 wells, or more), of a silicon wafer, of a chip, of a mass spectrometry target, or of a matrix.

In a further embodiment, the invention relates to an assay or protein biochip for identifying and characterising a high-affinity binder for the respective marker sequences, characterised in that an arrangement or assay a.) is brought into contact with at least one high-affinity binder, and b.) an interaction is detected by means of a signal, wherein at least one locus (spot) has a panel of marker sequences, obtainable by the method according to the invention.

In a preferred variant of the invention the high-affinity binder is at least one autoantibody, which identifies at least one panel of marker sequences obtainable by the method according to the invention, wherein, due to the autoantibody used in the sample of the method according to the invention, n–k marker sequences are provided in a panel. In particular, the marker sequences are preferably obtained from patients or test subjects suffering from an illness and correlate significantly to the prominence of such autoantibodies. For example, autoantibodies are particularly prominent, in patients suffering from autoimmune diseases, and corresponding autoantigens can be identified, characterised and selected by means of the method according to the invention and in particular can be provided in a panel of marker sequences.

Test subjects and patients can therefore advantageously be diagnosed or stratified in terms of the relevant, disease. Furthermore, personalised medication can be provided by producing a patient-individual panel of marker sequences, in which the patient's own tissue (biological material) is used as starting material for example.

The invention therefore likewise concerns panels of n–k marker sequences, obtainable by the method according to the invention, on a solid substrate, wherein the n–k marker sequences correlate with a single signal and are presented at a locus, and the marker sequences are specific autoantigens that bind specifically to the complementary autoantibodies of a sample containing autoantibodies.

In a further embodiment the invention relates to the diagnosis or stratification of diseases by means of a panel of marker sequences, wherein the marker sequences for example are autoantigens, at a locus (spot) of a solid substrate, wherein a sample containing autoantibodies is brought into contact and an interaction is detected by means of a single signal.

A locus (spot) is preferably arranged on a solid substrate. The locus may correspond to a well in a microtiter plate or to a grid point in the Luminex assay. The locus is the test field in which the panel of marker sequences is located and is designed in terms of its dimensions, topography and the used material such that the marker sequences can be applied and brought into contact with the high-affinity binder, and a single signal can be generated and measured.

The invention also relates to a singleplex assay comprising a panel of 2 or more different marker sequences having sufficient sensitivity on a locus or spot, wherein the different marker sequences can bind to one or more high-affinity binders and a single signal is thus obtained for detection of the high-affinity binder(s).

An embodiment of the invention concerns a singleplex assay, wherein 10 or 50 or 100 or more, preferably 6, 7 or 8, particularly preferably 3, 4 or 5, different marker sequences are combined and thus form the panel of different marker sequences.

A further embodiment of the invention concerns a singleplex assay, wherein the different marker sequences are obtained by the method according to the invention. The invention preferably concerns an embodiment in which the marker sequences for the singleplex assay are selected from antigens, parts of antigens, haptens or proteins.

The invention also relates to the use of a singleplex assay for early detection and/or diagnosis and/or stratification of a disease.

The invention also relates to a kit for the early detection and/or diagnosis and/or stratification of diseases, said kit containing a panel of marker sequences on a substrate that have been identified in accordance with the method according to the invention, or containing a singleplex assay according to the invention and further conventional aids (detection reagents, etc.). In a particularly preferred embodiment of the invention, antigens, in particular autoantigens, are used as marker sequences. A specific embodiment concerns the use of the kit in the case of autoimmune diseases or suspicion of autoimmune diseases (early detection.).

Diseases include any human diseases, preferably such as cancer, autoimmune diseases, in particular rheumatoid arthritis and multiple sclerosis among others, preferably diseases that have characteristic autoantibodies or patterns of autoantibodies, preferably in the plasma or serum.

Once the high-affinity binder contacts the panel of marker sequences at a locus (spot), the success of the binding process is evaluated, for example with use of commercially available image analysis software (GenePix Pro (Axon Laboratories), Aida (Raytest), ScanArray (Packard Bioscience).

Interactions according to the invention (for example protein at marker sequence, such as antigen/antibody) or suitable "means for detecting success of a binding process" or "means for detecting an interaction by means of signals" can be implemented in the usual manner, for example by means of fluorescent labelling, biotinylation, radioisotope labelling or colloidal gold or latex particle labelling. Bound antibodies are detected with the aid of secondary antibodies that are labelled by commercially available reporter molecules (for example Cy, Alexa, Dyomics, FITC or similar fluorescent dyes, colloidal gold or latex particles), or by reporter enzymes, such as alkaline phosphatase, horseradish peroxidase, etc. and the corresponding calorimetric, fluorescent or chemoluminescent substrates. The result is read out for example by means of a microarray laser scanner, a CCD camera, or visually.

Signals for detecting an interaction may further be determined with the aid of radioactive or fluorescently labelled antibodies, in particular by means of bioanalytical methods, such as Western blot (1D and 2D), immunohistochemistry, antibody arrays, Luminex®, ELISA, immunofluorescence, radioimmunoassays or mass spectrometry methods, such as MRM (multi reaction monitoring) or AQUA (absolute quantification).

Figure 1:
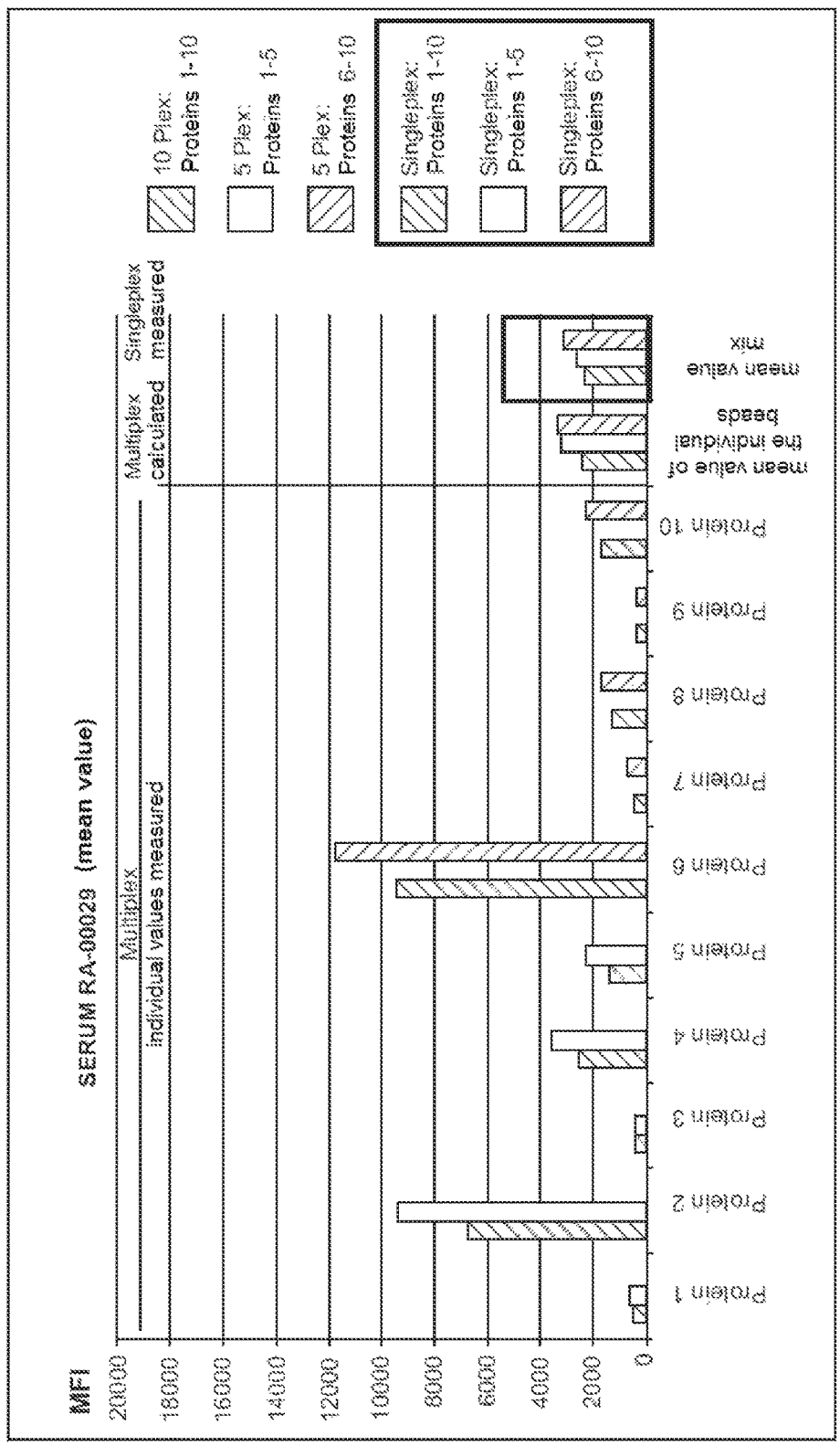
FIGS. 1 to 4 show the mean value MFIs of a multiplex assay (a number of marker sequences deliver a number of individual signals) and singleplex assays in comparison, wherein 10 different antigens (proteins 1 to 10) and the serums RA00029 (FIG. 1), RA0037 (FIG. 2), RA00046 (FIG. 3) and PRO244 (FIG. 4) were used. The individual values for proteins 1 to 10 were measured in the multiplex assay and the mean values tar the multiplex assay were calculated from this and compared with the measured value (single signal) for the singleplex assay.

The invention will be explained hereinafter by examples. The invention is not limited to the examples however, and in principle high-affinity binders, types of assays and detection methods can be applied universally for a wide range of marker sequences.

ELISA and PUPA Luminex assays are used in the examples in addition to antigens (proteins) as marker sequences and also serums that contain antigens and autoantigens as high-affinity binders.

Assays based on Luminex technology allow the simultaneous quantitative determination of up to 100 parameters in an individual sample, wherein multiplex assays are known in the prior art. Advantages of the multiplex format are high sensitivity and specificity, exact quantification and suitability for automation.

A preferred embodiment of the invention concerns singleplex assays (single-signal assays). In the singleplex assay (single-signal assay) according to the invention, only one parameter is determined in contrast to the multiplex assay. In the singleplex assay according to the invention, it is not a selected marker sequence that is used, but a panel of marker sequences obtained by combining a plurality of marker sequences to form a single marker (panel, of markers, marker combination). An advantage with the use of a panel of marker sequences in a singleplex assay is the additional signal amplification caused by the combination of the marker sequences in a single panel. In the singleplex assay, the mean value of the intensity of the combined marker sequences is then preferably measured. Marker sequences will also be referred to hereinafter simply as markers.

Example 1: Additional Signal Amplification by Marker Combination in a Single Panel of Marker Proteins Theoretical signal intensity, preliminary consideration In a singleplex assay with a panel of marker sequences formed from protein 1 and protein 2 (2-way combination), in which protein 1 has a signal intensity of 10,000 and protein 2 has a signal intensity of 30,000, the calculated mean value of the intensity MFI of the signals from protein 1 and protein 2 is 20,000.

In a singleplex assay with a 5-way combination of protein 1, protein 2, protein 3, protein 4 and protein 5 in a panel, the calculated signal intensity of the panel of marker sequences corresponds to the mean value of the individual signals of the 5 proteins.

Test Execution

The used beads are coated with the proteins acting as antigen. These coated beads are incubated with different serums, such that the antibodies present in the serum can bind to the antigens. This involves comparing the signal intensities of a multiplex measurement with the signal intensity of the singleplex measurement according to the invention.

In the multiplex assay 10 different bead regions are coated with 10 different proteins, wherein 100 beads/bead region, that is to say a total of 1,000 beads, are used. 45 serums (each replicated twice) are then tested in three different settings: as 10 Plex with the proteins 1-10 and as 5 Plex, once with the proteins 1-5 and once with the proteins 6-10. When evaluating the data, the median MFI (median fluorescent intensity) or mean value MFI (mean fluorescent intensity) of all proteins is determined.

In the singleplex assay 10 proteins are tested in the same bead region, wherein 1,000 are located in a bead region. 45 serums (each replicated twice) are tested in 3 settings: as singleplex with the proteins 1-10, as singleplex with the proteins 1-5 and as singleplex with the proteins 6-10. When evaluating the data, the median MFI or mean value MFI of the 1,000 beads (mix) is taken into consideration.

The principle of the measurement and evaluation is based on Luminex technology. The beads are coloured using two fluorescent dyes (red and infrared), which emit in different ranges of the optical spectrum. The combination of these two dyes in ten different concentration stages in each case leads to one hundred shades of red and infrared that are spectrally distinguishable. Each of the resultant fluorescent intensities defines a population of bead regions. The fluorescent coding of the bead regions forms the basis for the identification by the analysis device and the precise assignment. The clear assignment of the individual bead regions is the basis for the multiplex analysis, wherein each bead region represents an individual test (fluorescent coding of the head regions). In the singleplex only one head region is used, such that an individual test is carried out and neither an assignment nor labelling with the red and infrared fluorescent dye is necessary, in contrast to the multiplex assay.

The beads are coated with the proteins 1 to 10 to be tested, said proteins acting as antigen. The beads are then incubated with the serums to be tested. The better the extent to which the antibodies present in a serum bind to the antigen (s) immobilised on the bead (marker proteins), the higher is the measured fluorescent signal. The specific detection of the binding of the antibody to the heads is achieved via a detection molecule (conjugate). This conjugate has a high specific affinity to the bound antibody from the serum and is coupled to a fluorescent dye (for example phycoerythrin), which emits in the wavelength range of green light. This spectral range differs from those of the internal dyes, such that the classification of the beads and the quantification of the antibodies can be executed in parallel in the multiplex assay.

Evaluation of the Results:

The general standard evaluation for the measurement of Luminex beads is the median MFI (median fluorescent intensity). Here, individual high and/or low signals are ignored systematically.

The median splits the total quantity (number) of measured intensities into two halves. The median is therefore the intensity value that lies in the middle of all measured intensities. It specifies the average intensity of the measured intensities, that is to say the "typical" intensity for a specific protein, here a specific antibody. With the specification of the median, only the average value is taken into consideration, whereas individual high and low intensity signals that lie to the right and left of the median remain unconsidered.

The mean value "M" (arithmetic mean) is calculated as follows:

$$M = 1/n \Sigma Xi = x1 + x2 + \ldots + xn/n$$

For the multiplex measurement of a protein 1 on bead 1 (signal intensity 300), protein 2 on bead 2 (signal intensity 600) and protein 3 on bead 3 (signal intensity 30,000), a calculated median of 600 MFI (median fluorescent intensity) and a calculated mean value of 10,300 MFI (mean fluorescent intensity) are thus given.

For a singleplex measurement of protein 1 (signal intensity 300), protein 2 (signal intensity 600) and protein 3 (signal intensity 30,000) on a head, the measured median is 600 MFI and a measured mean value is 10,300 MFI.

The values of median MFI and mean value MFI in the multiplex and singleplex assay are consequently identical.

In the singleplex measurement according to the invention, some high signals should not be ignored, in contrast to the conventional multiplex measurement. With the singleplex measurement according to the invention, the mean value is therefore preferably determined, and not the median.

In FIG. 1, the MFI mean values of the individual proteins 1 to 10 of the multiplex assay are illustrated. The mean values of the multiplex assay for proteins 1-10, 1-5 and 6-10 have been calculated from these values. These calculated mean values of the multiplex assay were compared with those from the measured values of the singleplex assay for proteins 1-10, 1-5 and 6-10.

The following serums were tested: RA-00037 (positive), RA-00029 (positive), RA-00046 (positive) and PRO-244 (negative). In the case of serum RA-00029 it was found that the calculated mean values of the multiplex assay coincide largely with the measured mean values of the singleplex assay (that is to say are comparable), more specifically for proteins 1-10 and also for proteins 1-5 and 6-10.

Figure 2:
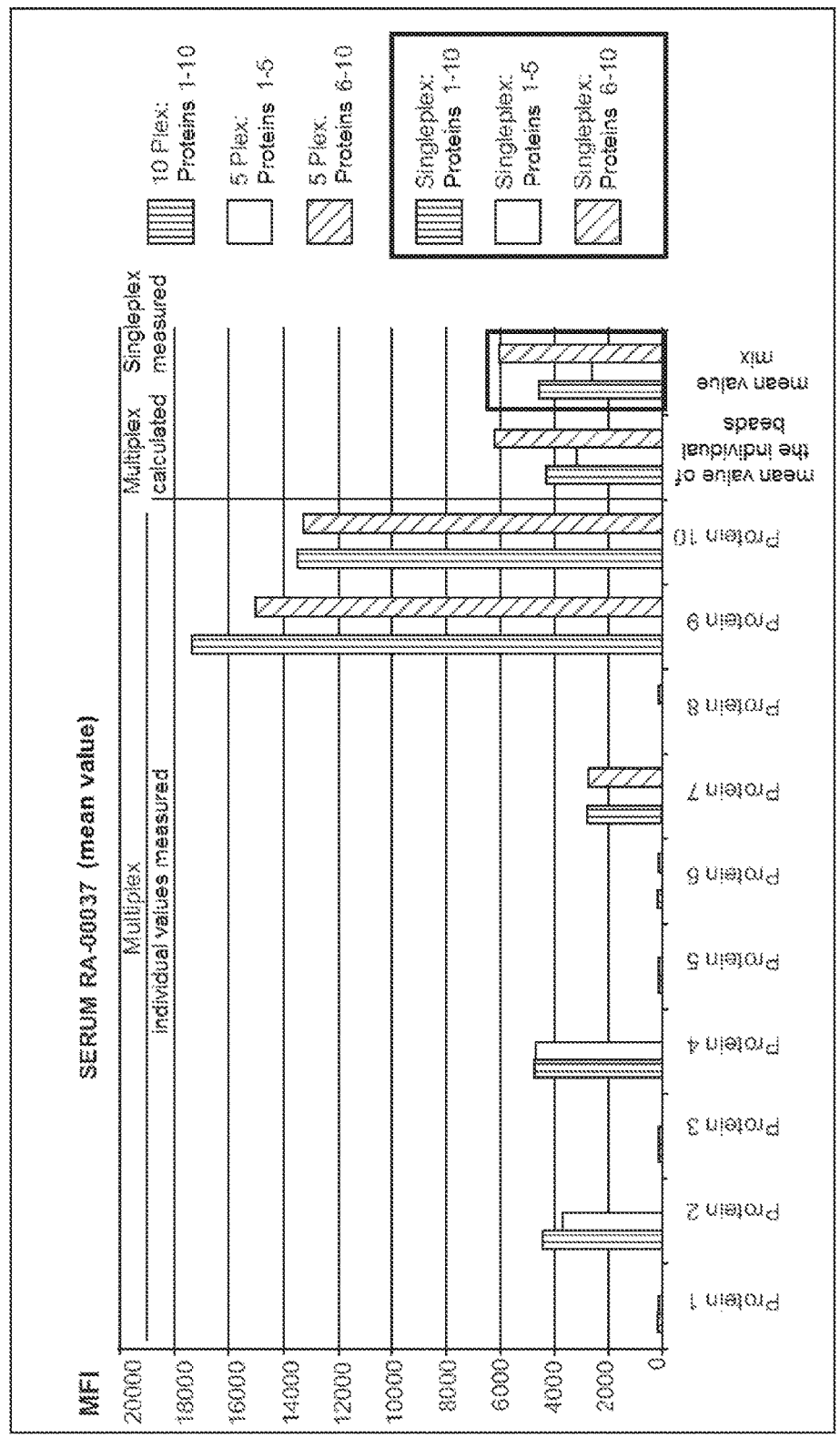

Similar effects were found for serums RA-00037 (FIG. 2), RA-00046 (FIG. 3) and PRO-244 (FIG. 4)—the mean values of the multiplex assay calculated from the measured intensities are comparable with the measured intensities of the singleplex assay (evaluation on the basis of mean values).

These experiments have shown that the mean value MFI of the multiplex assay (proteins on different bead regions) as 5 plex and as 10 plex is comparable to the mean value of the respective singleplex assay (protein panel on one bead region).

Example 2: Comparison of Multiplex Assay and Singleplex Assay with Respect to the Median Intensities and the Mean Value Intensities Test set-up and execution as in example 1 with protein 1 on bead 1, protein 2 on bead 2 and protein 3 on bead 3 in the multiplex assay. The median MFI and mean value MFI were determined once for the multiplex assay from the measured intensities of proteins 1 to 3.

These were compared with the measured intensities of the median MFI and the mean value MFI of the singleplex assay. In the singleplex assay, proteins 1, 2 and 3 were immobilised on a single bead (bead 4).

Figure 5:
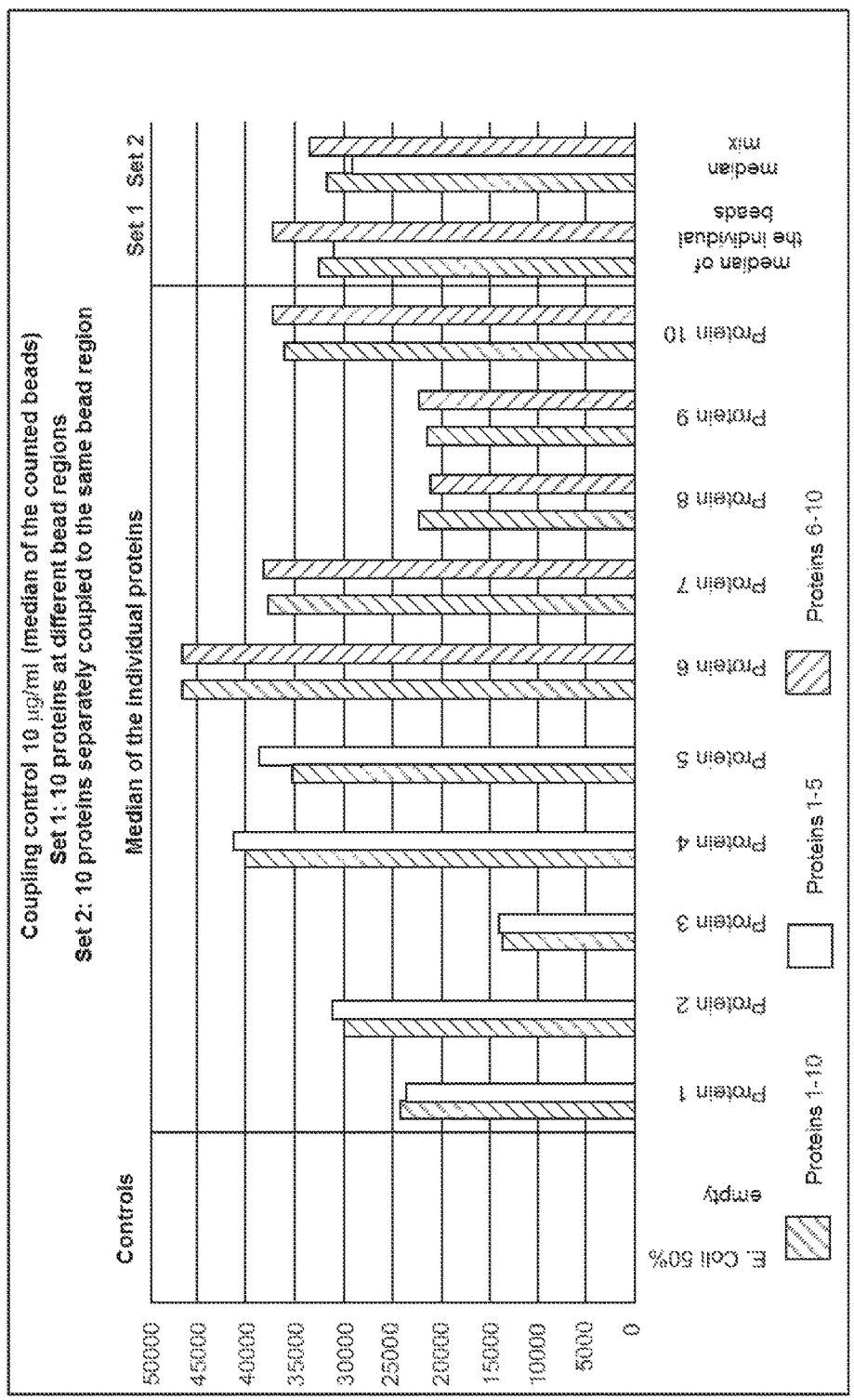
FIG. 5 shows the comparison of the median MFIs of multiplex and singleplex assay, wherein 10 different antigens (proteins 1 to 10) were used. 10 µl/ml (median of the counted heads) were used as a coupling control. Set 1 (multiplex assay) with 10 proteins at different bead regions is compared with set 2 (singleplex assay) with 10 proteins at the same bead region.

FIG. 5 shows the comparison of the median of multiplex and singleplex assay of individual proteins 1 to 10. In set 1 the proteins 1-10, 1-5 and 6-10 are coupled to different bead regions, and in set 2 proteins 1 to 10, 1-5 and 6-10 are coupled separately to the same bead region. The values for the median MFI of the multiplex and singleplex assays are practically identical for proteins 1 to 10, 1-5 and 6-10. 10 µg/ml (median of the counted beads) were used as a coupling control.

Figure 6:
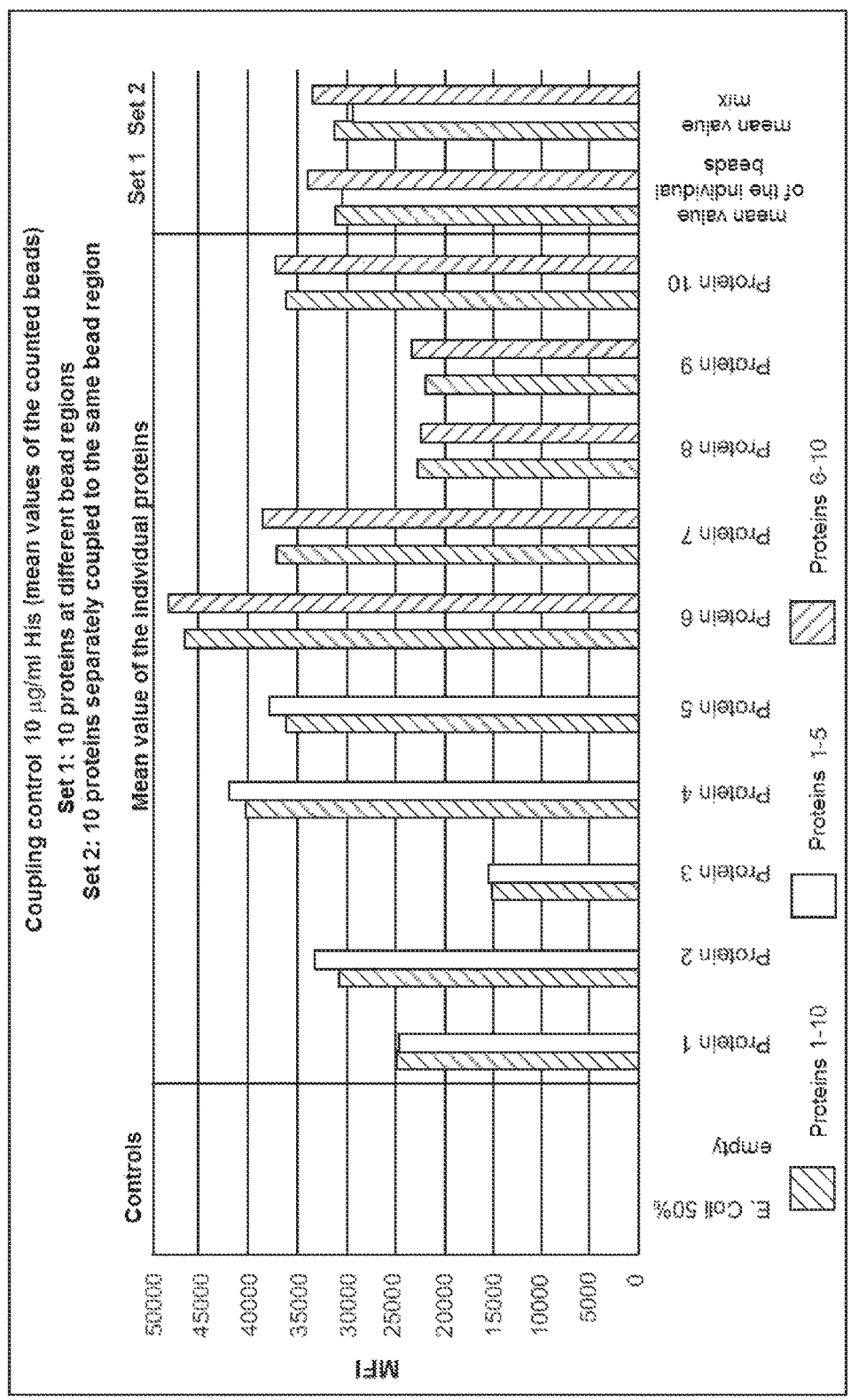
FIG. 6 shows the comparison of the mean value MFIs of multiplex and singleplex assay, wherein 10 different antigens (proteins) were used. 10 µl/ml (mean value of the counted beads) were used as a coupling control. Set 1 (multiplex assay) with 10 proteins at different bead regions is compared with set 2 (singleplex assay) with 10 proteins at the same bead region.

FIG. 6 shows the comparison of the mean value of the multiplex and singleplex assay of individual proteins 1 to 10. In set 1 proteins 1-10, 1-5 and 6-10 are coupled to different bead regions, and in set 2 proteins 1 to 10, 1-5 and 6-10 are coupled separately to the same bead region. The values both for the mean value MFI of multiplex and singleplex assay are practically identical. 10 µg/ml (mean value of the counted beads) were used as a coupling control.

Example 3: SUPA Microarray Evaluation

The signal intensities of multiplex and singleplex assay were compared. The way in which the signal intensity changes with a reduction of marker sequences by the combination of a plurality of marker sequences to form a single marker panel was examined.

The following consideration forms the starting point: the sum of signal intensities 15,000 and 5,000 gives a signal intensity of 20,000. The mean value of the signal intensity from 15,000 and 5,000 is a signal intensity of just 10,000.

Figure 11:
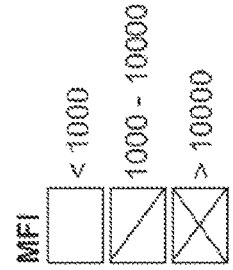
FIG. 11 shows the result of microarray experiments. The signal intensities of the used serums (RA0026 so RA0046) with the individual used marker sequences P1 to P9 and P0 are specified.

In microarray experiments the antigen/antibody interactions of 10 proteins and 20 serums were examined on protein microarrays (see FIG. 11). The examined antigens (proteins) are denoted by P1 to P0. The serums RA00026-RA00033, RA00035-RA00046 were examined for activity of autoantibodies contained in these serums.

On the whole, only low signal intensities were found for protein/autoantibody interactions in the individual serums, wherein the individual serums differ considerably in part in terms of their activity with respect to individual proteins and also signal intensity. Two very high signal intensities of 15,643 (with protein 9) and 16,034 (with protein 0) were found with the serum RA00037. On the whole, serum RA000333 demonstrated average activity—a signal intensity of 1,367 with protein 1, 1,573 with protein 3, 5,010 with protein 8 and 2, 631 with protein 9. Signal intensities with an MFI (median fluorescent intensity) of more than 10,000 are referred to as high signal intensities. Signal intensities with an MFI (median fluorescent intensity) from 1,000 to 10,000 are referred to as average signal intensity, and signal intensities with an MFI of less than 1,000 are referred to as low signal intensities.

The serums RA00037 and RA00033 were characterised further with respect to their reactivity to different protein combinations.

Table 2 gives an overview of the used protein combinations and the used naming system.

TABLE 2

| | Tested number | Naming system | Explanation |
|---|---|---|---|
| 1 Protein | 10 | P6 | Protein 6 |
| combination of 2 proteins | 45 | P67 | Proteins 6 and 7 |
| combination of 3 proteins | 20 | P678 | Proteins 6, 7 and 8 |
| combination of 4 proteins | 8 | P6789 | Proteins 6, 7, 8 and 9 |
| combination of 5 proteins | 2 | P67890 | Proteins 6, 7, 8, 9 and 0 |
| combination of 10 proteins | 1 | P1234567890 | Proteins 1, 2, 3, 4, 5, 6, 7, 8, 9 and 0 |

Serum RA00037 and Serum RA00033 were tested with the different proteins in the combinations specified in Table 2. 16 replicates per protein or protein mixture were tested. The threshold value at which the background differs from the signal was then determined statistically, and all signals below the threshold value (detection call) were set to 0. The detection call algorithm helps to decide whether or not a spot on a microarray is lit. To this end, the distribution of the local background over the microarray is calculated.

In each case 5% at the lower end (lowest values) and 5% of the upper end (highest values) are removed from this distribution. The rest of the data is then logarithmised to the base of 10.

The threshold value is given from she mean value of the logarithmised data plus twice she standard deviation of the logarithmised data.

All spots of which the intensities lie below this value are set to zero.

Figure 7:
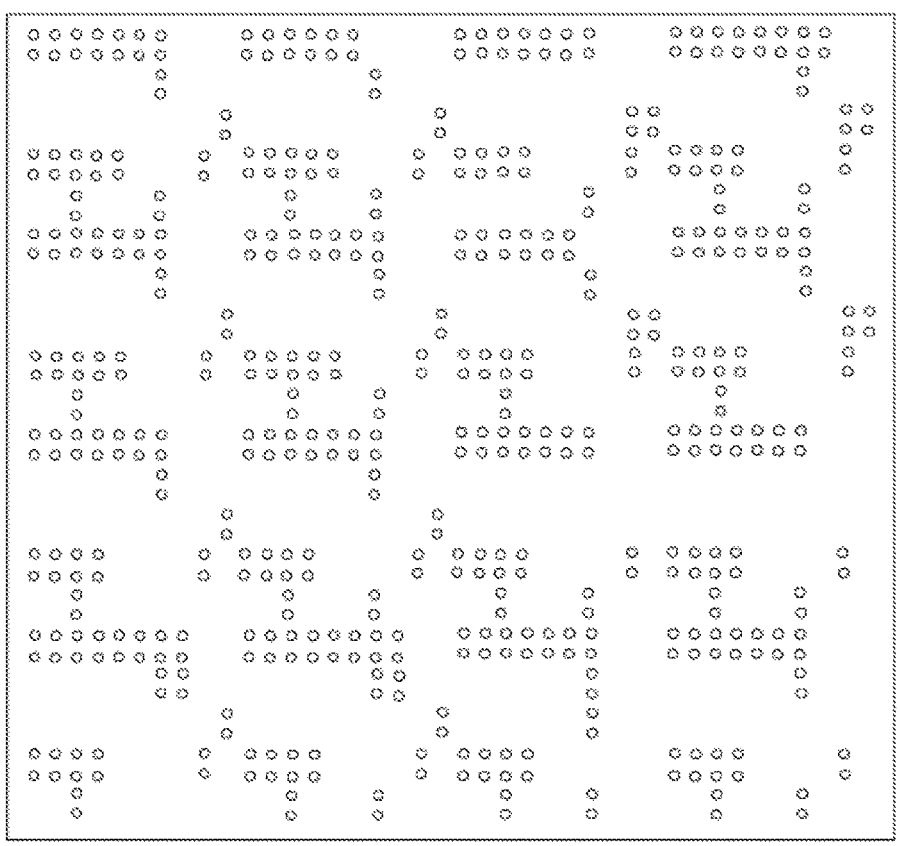
FIG. 7 shows the spots on a microarray on which proteins and protein mixtures (marker sequences) are immobilised, said proteins acting as antigens and having been incubated with serum. RA00037.
Figure 8:
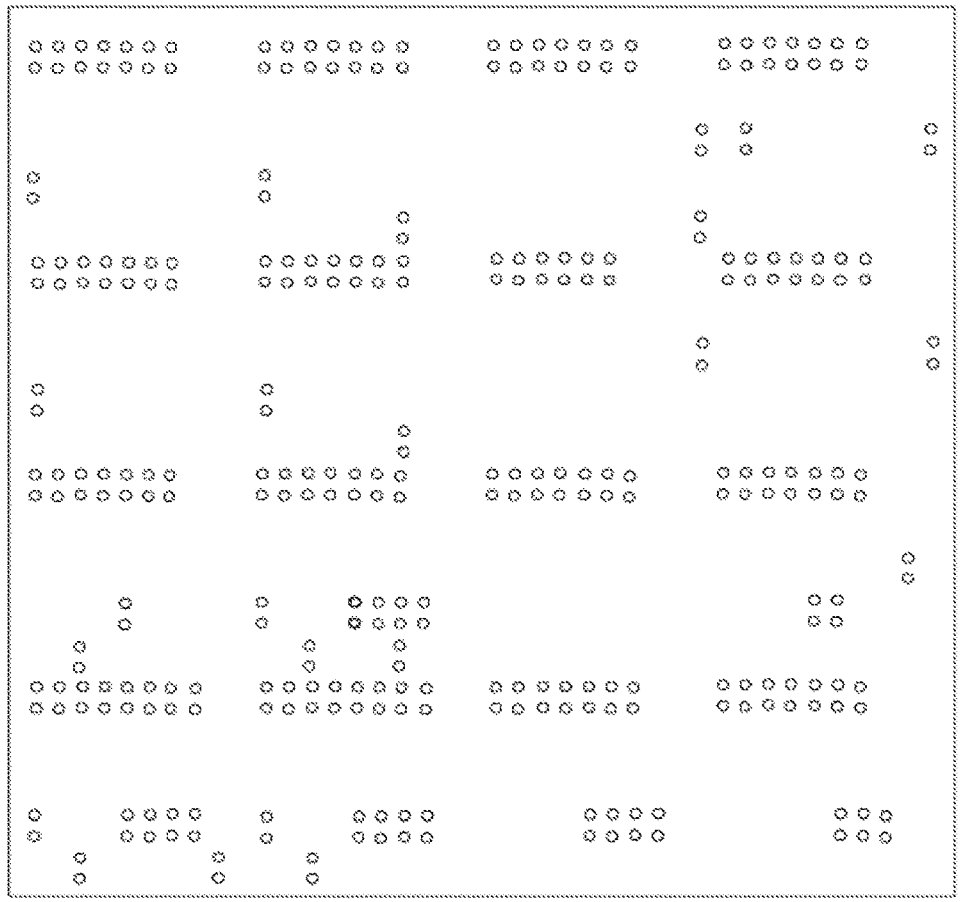
FIG. 8 shows the spots on a microarray on which proteins and protein mixtures (marker sequences) are immobilised, said proteins and protein mixtures acting as antigens and having been incubated with serum RA00033.

With the serum RA00037, the strongest signal was measured with a signal strength of 16034 with P0 (FIG. 7). The background, with a signal strength of 1134 and the dynamic range, thus lies at 1.15—in other words between log 10(1134) and log 10(16034). On the whole, 35 different interactions were detected in the case of RA00037 and the used protein combination.

Figure 3:
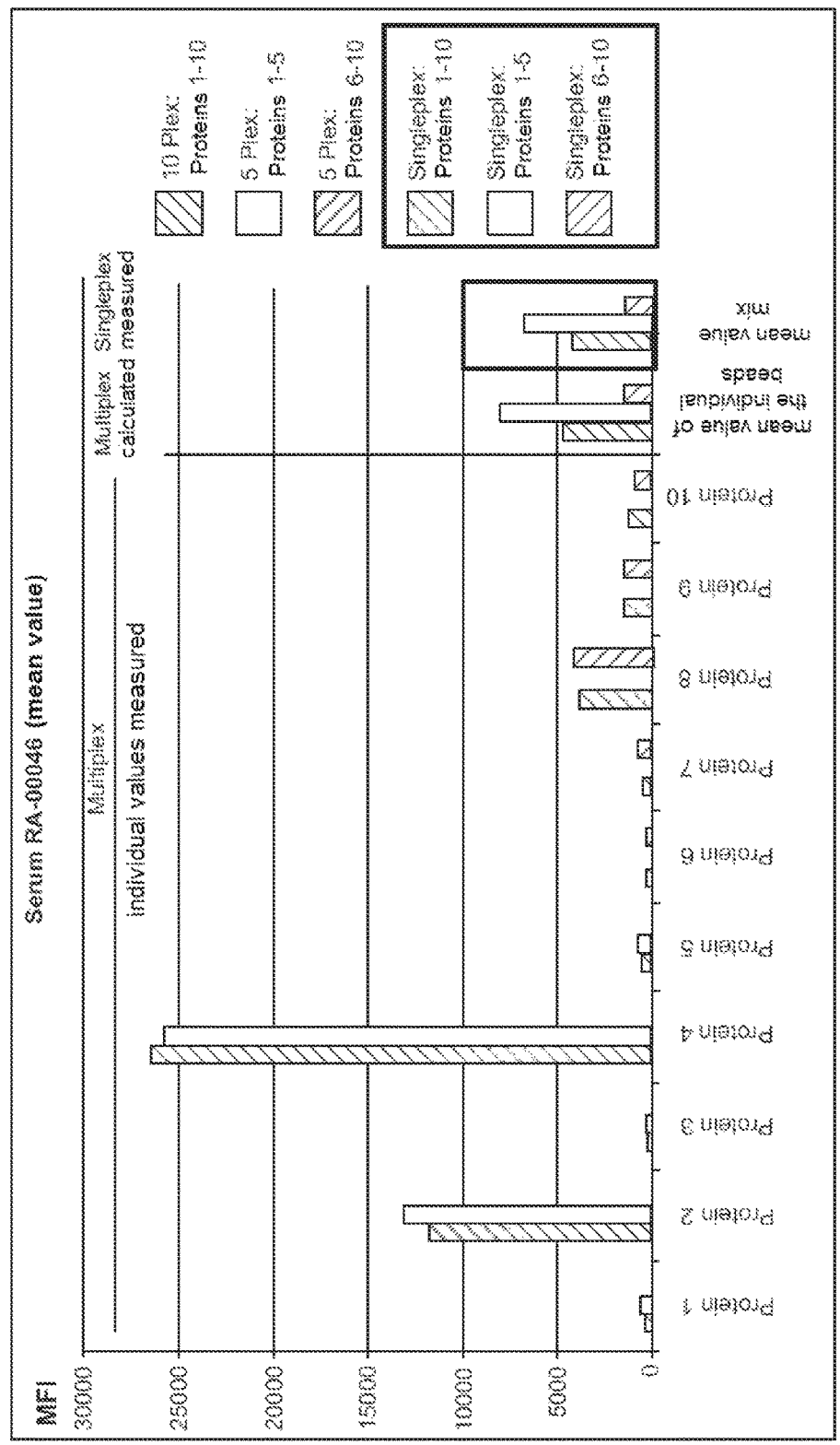
Figure 4:
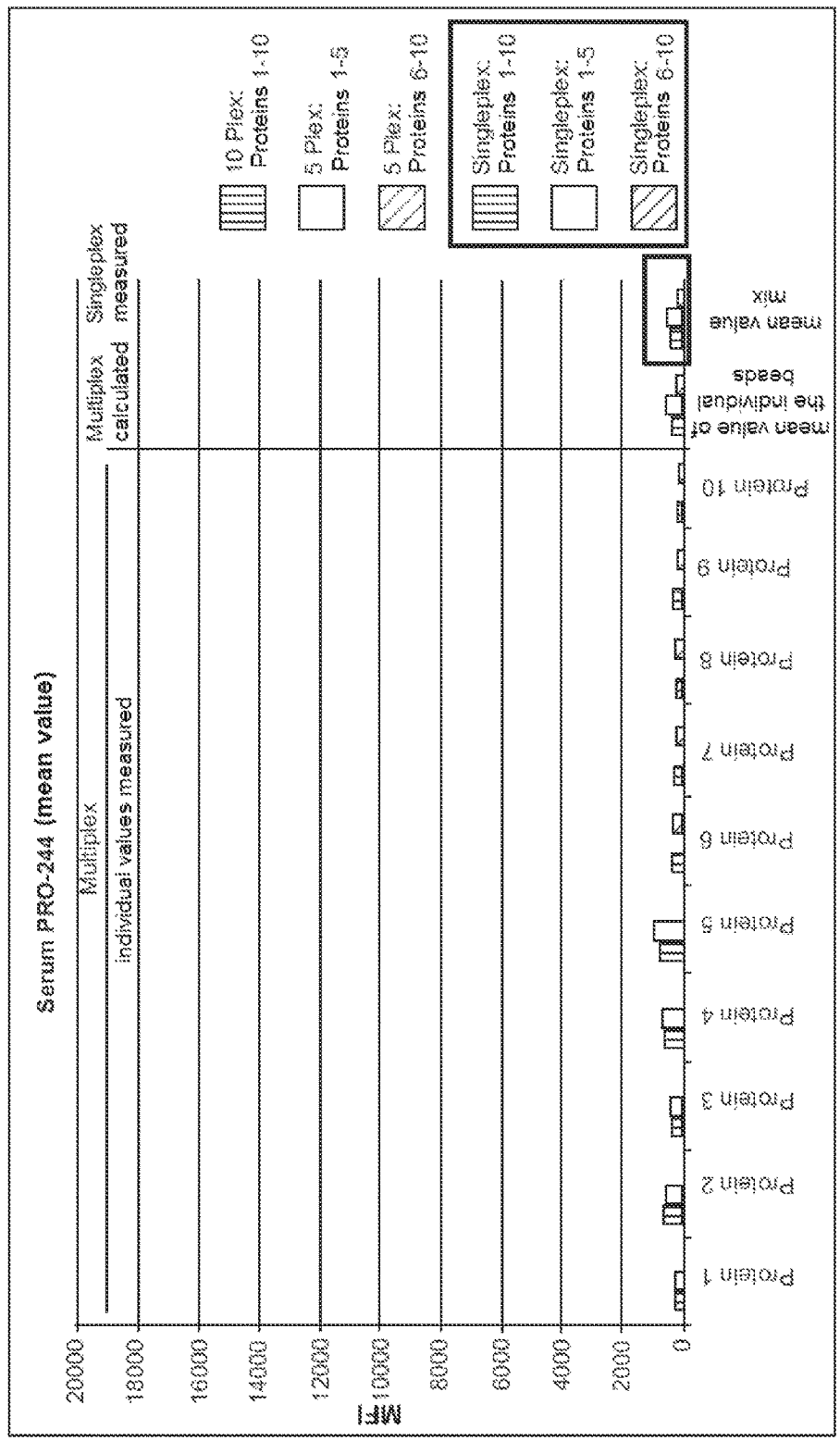

With serum RA00033, the strongest signal was measured with a signal strength of 5010 with P8 (FIG. 3). The background, with a signal strength of 1522 and the dynamic range, thus lies at 0.52—in other words between log 10(1522) and log 10(5010). On she whole, 38 different interactions were detected in she case of RA00033 and the used protein combination.

A detailed analysis of the produced signal intensities of the proteins and protein combinations by interaction with autoantibodies in serums RA00037 and serum RA00033 is shown in Table 3.

TABLE 3

| Naming system | Serum RA00037 signal intensity MFI | Naming system | Serum RA00033 signal intensity MFI |
|---|---|---|---|
| P6 | 0 | P6 | 0 |
| P7 | 0 | P7 | 0 |
| P8 | 0 | P8 | 5010 |
| P9 | 15643 | P9 | 2631 |
| P0 | 16034 | P0 | 0 |
| P60 | 5236 | P68 | 2218 |
| P70 | 4059 | P78 | 2121 |
| P80 | 5373 | P89 | 3196 |

TABLE 3-continued

| Naming system | Serum RA00037 signal intensity MFI | Naming system | Serum RA00033 signal intensity MFI |
|---|---|---|---|
| P90 | 9856 | P80 | 1653 |
| P670 | 2210 | P678 | 0 |
| P680 | 2490 | P689 | 1809 |
| P690 | 4344 | P680 | 900 |
| P780 | 2014 | P789 | 2331 |
| P790 | 5292 | P780 | 0 |
| P890 | 4783 | P890 | 926 |
| P6790 | 3118 | P6789 | 976 |
| P6890 | 2455 | P6890 | 0 |
| P7890 | 2893 | P7890 | 978 |
| P67890 | 2240 | P67890 | 0 |
| P1234567890 | 0 | P1234567890 | 0 |

Figure 9:
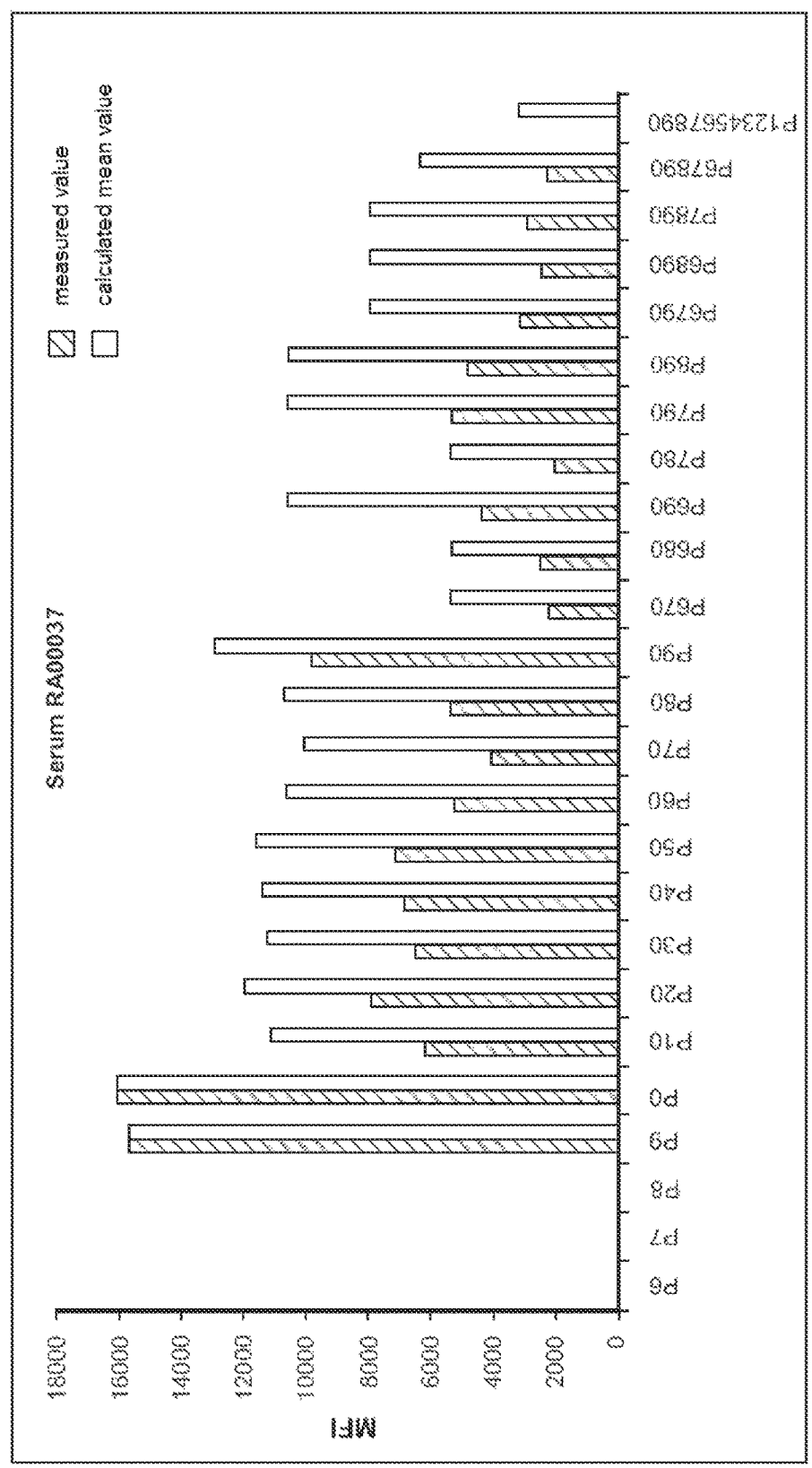
FIG. 9 shows the calculated mean value compared with the measured value of the signal intensities with use of serum RA00037 with different proteins and protein mixtures as marker sequence or panel of marker sequences.
Figure 10:
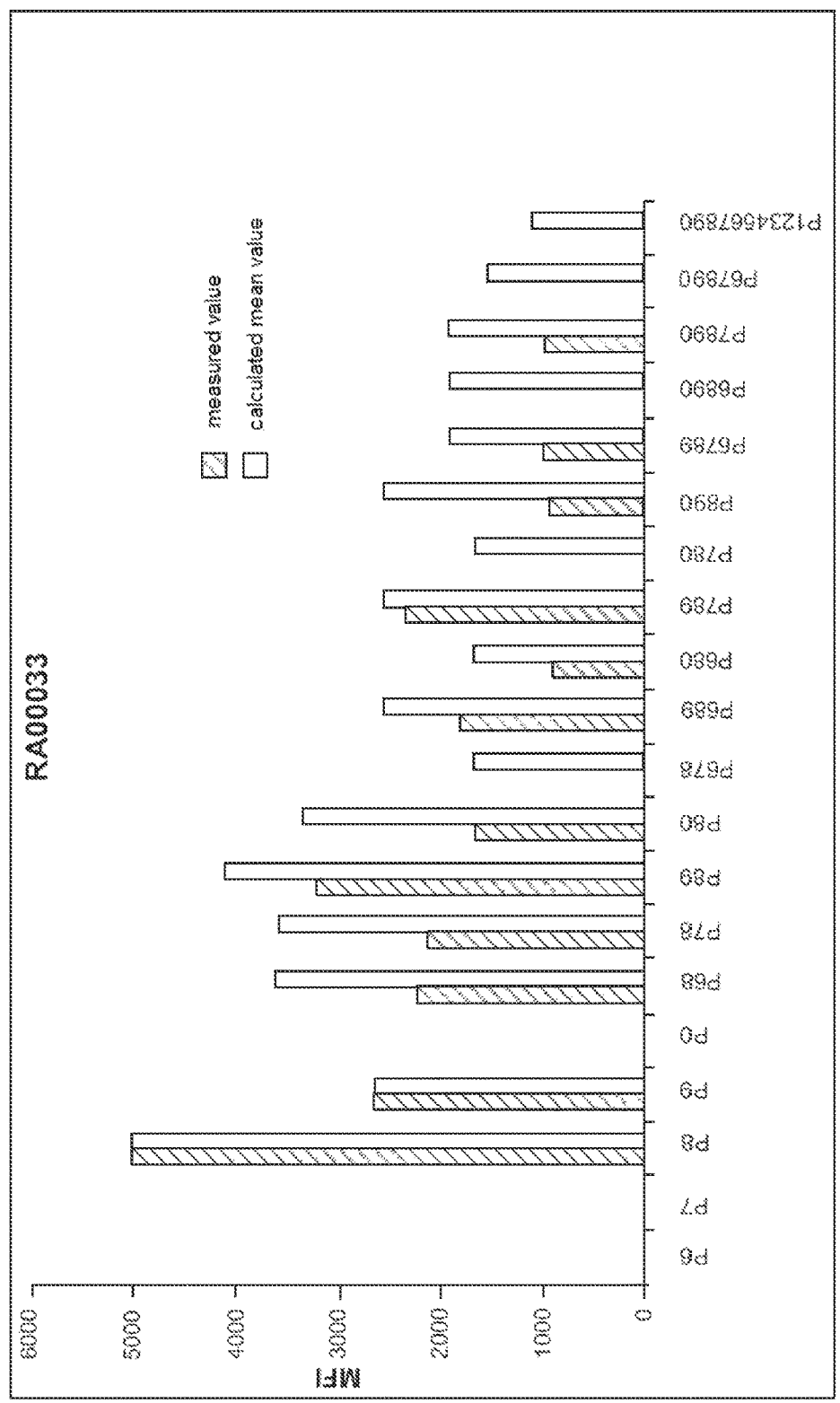
FIG. 10 shows the calculated mean value compared with the measured value of the signal intensities, with use of serum RA00033 with different proteins and protein mixtures as marker sequence or panel of marker sequences.

FIG. 9, for serum RA00037, shows the calculated and measured MFIs for the individual proteins and protein combinations in comparison. FIG. 10 shows the same for RA00033.

It has been found that, with the combination of many proteins, the signal strength decreases and the measured signal intensities lie below the calculated signal intensities. For the serums RA00037 and RA00033 tested here, signals can no longer be detected with the combination of 10 proteins in one bead region. With a combination of 5 proteins, signals can be detected, however the detected signal intensity lies below the calculated signal intensities. With the used serums and marker panels, panels of 2 to 3 proteins are optimal. In particular, proteins that demonstrate strong interaction with autoantibodies are suitable for use in a marker panel.

Example 4: Singleplex Assay as SUPA-ELISA (ELISA Multimarker)

The advantages of the ELISA are the low costs, simple application (ELISA applications are known and standardised) and the comparatively quick execution.

ELISAs (enzyme-linked-immunoabsorbent assays) have long been known (for example "Immunoassays of endogenous plasma insulin in man", Rosalyn S. Yalow and Solomon A. Berson, From the Radioisotope Service, Veterans Administration Hospital, New York, N.Y., Submitted for publication Mar. 7, 1960; accepted Mar. 22, 1960; *J. Clin. Invest.* 39: 1157-75, doi:10.1172JCI104130. PMC 441860. PMID 13346364; "Enzyme-linked immunosorbent assay (ELISA) Quantitative assay of immunoglobulin G" in Immunochemistry, Pergamon Press 1971, Vol. 8 pp. 871-874).

Here, the indirect ELISA is used, described for example in (http:en.wikibooks.org/wiki/Structural_Biochemistry/Protein/Enzyme-Linked_Immuniabsorbent_Assay_%28ELISA%29). Here, an indentation in an ELISA plate (well) is coated with a protein, which acts as an antigen. A specific antibody can bind thereto. The binding is detected by a second (enzyme-linked) antibody, which converts a detectable substrate.

In a singleplex ELISA according to the invention, 10 proteins as antigen are placed in a well of an ELISA plate and the signal of the panel of antigens is determined.

The proteins used as antigens are immobilised overnight (3 times per sample). The proteins are then washed, blocked for two hours with Candor buffer, then washed and incubated for one hour with the serum to be tested. A washing step then follows as well as subsequent incubation for one hour with human AK HRP conjugate. The proteins are then washed again and incubated with substrate for 15 min. The reaction is stopped after 15 min and the result is read out at 450 nm. (Readout Tecan Safire).

Three different serums RA00029, RA00037 and RA00045 are tested.

The serums deliver the same results as in the Luminex assay (Examples 2 and 3). It is necessary to optimise the nest conditions for the ELISA for the marker proteins to be tested and for the serums to be analysed, for example in respect of the used buffer and the coating of the ELISA plates.

The singleplex assay can be used universally, wherein the conditions have to be optimised for the respective assay type and the used detection system in order to obtain a significant single signal of the panel of marker sequences.

The invention claimed is:

1. A method for the identification and/or selection of marker sequences suitable for use in a singleplex assay for detection and/or diagnosis and/or stratification of a disease in a subject, comprising the following steps:
    a) mixing n marker sequences placed on a solid substrate with a sample containing high-affinity binders and detecting a single signal resulting from the interactions between the n marker sequences and the high-affinity binders,
    b) mixing at least n–1 marker sequences having statistically sufficient signal intensity identified from a) with said sample containing high-affinity binders and detecting a single signal resulting from the interaction between the at least n–1 marker sequences and the high-affinity binders,
    c) optionally repeating step b) with at least n–k marker sequences, wherein k>1, and
    d) selecting n–k marker sequences having statistically sufficient signal intensity identified from b) or c) for use in a singleplex assay for detection and/or diagnosis and/or stratification of a disease in a subject,
    wherein the n–k marker sequences selected in d) comprise at least 4 different marker sequences.

2. The method of claim 1, wherein the marker sequences are obtained from biological material.

3. The method of claim 2, wherein the biological material is selected from the group consisting of tissue, native sources, cells, bacteria, viruses, phages, prions, plants, animals and humans.

4. The method of claim 1, wherein the marker sequences are mRNA, si-RNA, microRNA, cDNA, peptide, protein, or originate from an expression library.

5. The method of claim 4, wherein the protein is an antigen or an autoantigen.

6. The method of claim 4, wherein the expression library is an mRNA, si-RNA, microRNA, cDNA, peptide or protein expression library.

7. The method of claim 1, wherein the high-affinity binders are antibodies.

8. The method of claim 1, wherein the high-affinity binders are autoantibodies.

9. The method of claim 1, wherein the n-k marker sequences selected in d) are applied to a substrate.

10. The method of claim 9, wherein the substrate is a filter, a membrane, a magnetic or fluorophore labelled bead, a silicon wafer, glass, metal, plastic, a chip, a mass spectrometry target or a matrix.

11. The method of claim 1, wherein the sample containing high-affinity binders is a bodily fluid or tissue extract.

12. The method of claim 11, wherein the high affinity binders are antibodies or autoantibodies and the bodily fluid is blood, whole blood, blood plasma, blood serum, patient serum, urine, cerebrospinal fluid, or synovial fluid.

13. The method of claim 1, wherein the signals are detected with the aid of radioactive or fluorescently labelled antibodies by means of a bioanalytical method or a mass spectrometry method, wherein the bioanalytical method is optionally Western blotting (1D and 2D), immunohistochemistry, antibody arrays, Luminex, ELISA, immunofluorescence, radioimmunoassays, and wherein the mass spectrometry methods are optionally MRM (multi reaction monitoring) or AQUA (absolute quantification).

14. The method of claim 1, wherein the n-k marker sequences selected in d) comprise at least 10 different marker sequences.

15. The method of claim 1, wherein the marker sequences are antigens, parts of antigens, haptens or proteins.

* * * * *